(12) United States Patent
Brother et al.

(10) Patent No.: US 6,234,988 B1
(45) Date of Patent: May 22, 2001

(54) HEEL LOCKING, ENERGY ABSORBING, SUPPORT AND CUSHIONING DEVICE

(75) Inventors: Theodore B. Brother, Andover; Michael D. Nichols, Gardner, both of MA (US)

(73) Assignee: I-Tek, Inc., Lawrence, MA (US)

( * ) Notice: Subject to any disclaimer, the term of this patent is extended or adjusted under 35 U.S.C. 154(b) by 0 days.

(21) Appl. No.: 09/461,987

(22) Filed: Dec. 15, 1999

(51) Int. Cl.[7] .................................................. A61F 13/00
(52) U.S. Cl. .............................. 602/65; 602/13; 602/23; 128/882
(58) Field of Search ................................. 602/65, 13, 23, 602/30; 128/882; 601/152; 2/239, 22, 240, 267

(56) References Cited

U.S. PATENT DOCUMENTS

| | | | |
|---|---|---|---|
| 4,252,910 | 2/1981 | Schaefer | 521/145 |
| 5,501,659 | * 3/1996 | Morris et al. | . |
| 5,596,770 | * 1/1997 | Kunesh | . |
| 5,833,639 | * 11/1998 | Nunes et al. | . |
| 5,869,164 | 2/1999 | Nickerson et al. | 428/76 |

* cited by examiner

Primary Examiner—Michael A. Brown
Assistant Examiner—Lalita M. Hamilton
(74) Attorney, Agent, or Firm—Nields & Lemack

(57) ABSTRACT

A heel locking, energy absorbing, support and cushioning device adapted to fit around at least a portion of a user's foot and ankle, comprising, a sleeve having one or more pockets at least partially fixed to the walls of the sleeve which are at least partially filled with a compressible, polymeric material, flowable at room temperature, capable of absorbing impact energy, and comprising a plurality of microspheres.

19 Claims, 3 Drawing Sheets

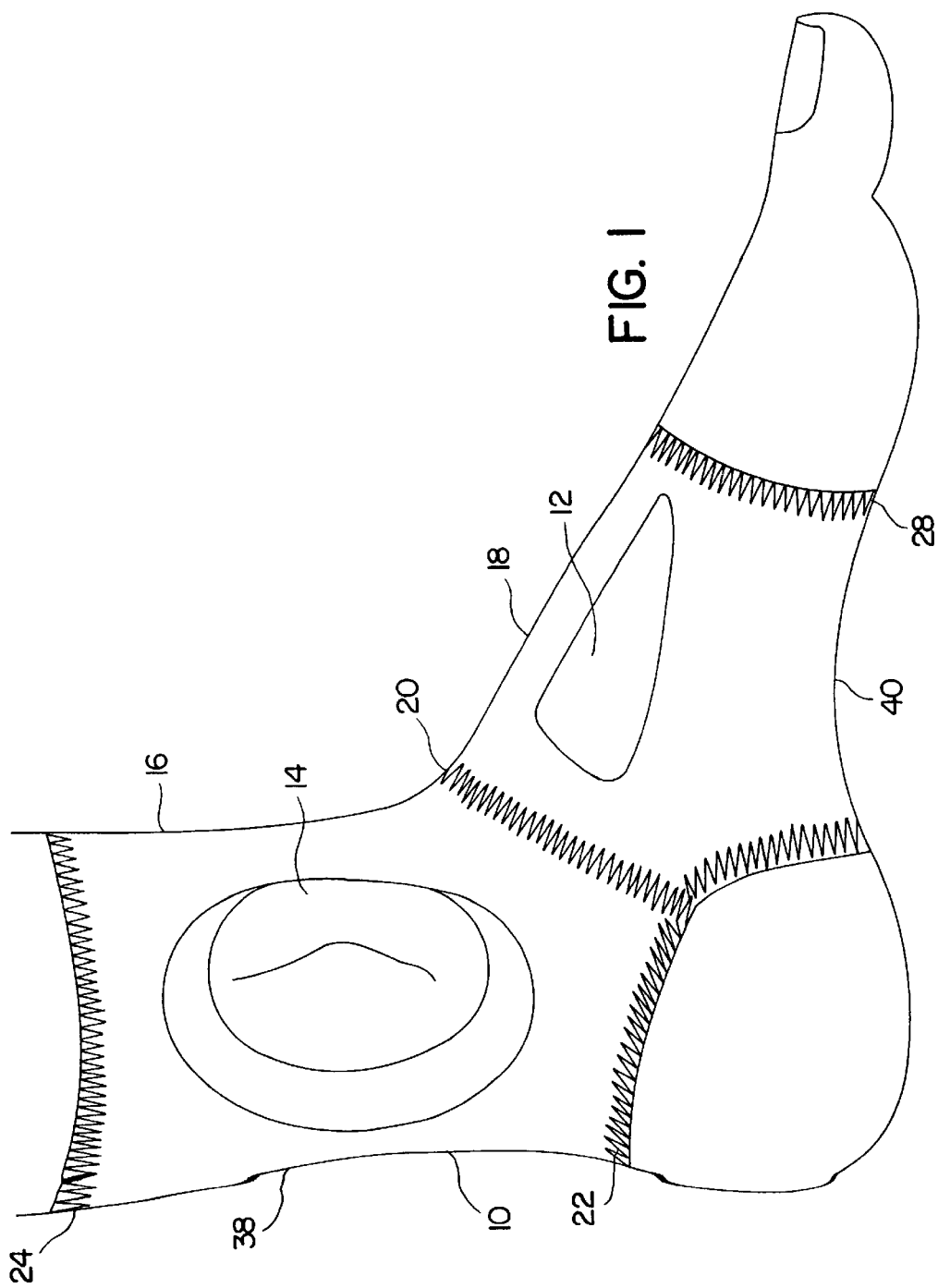

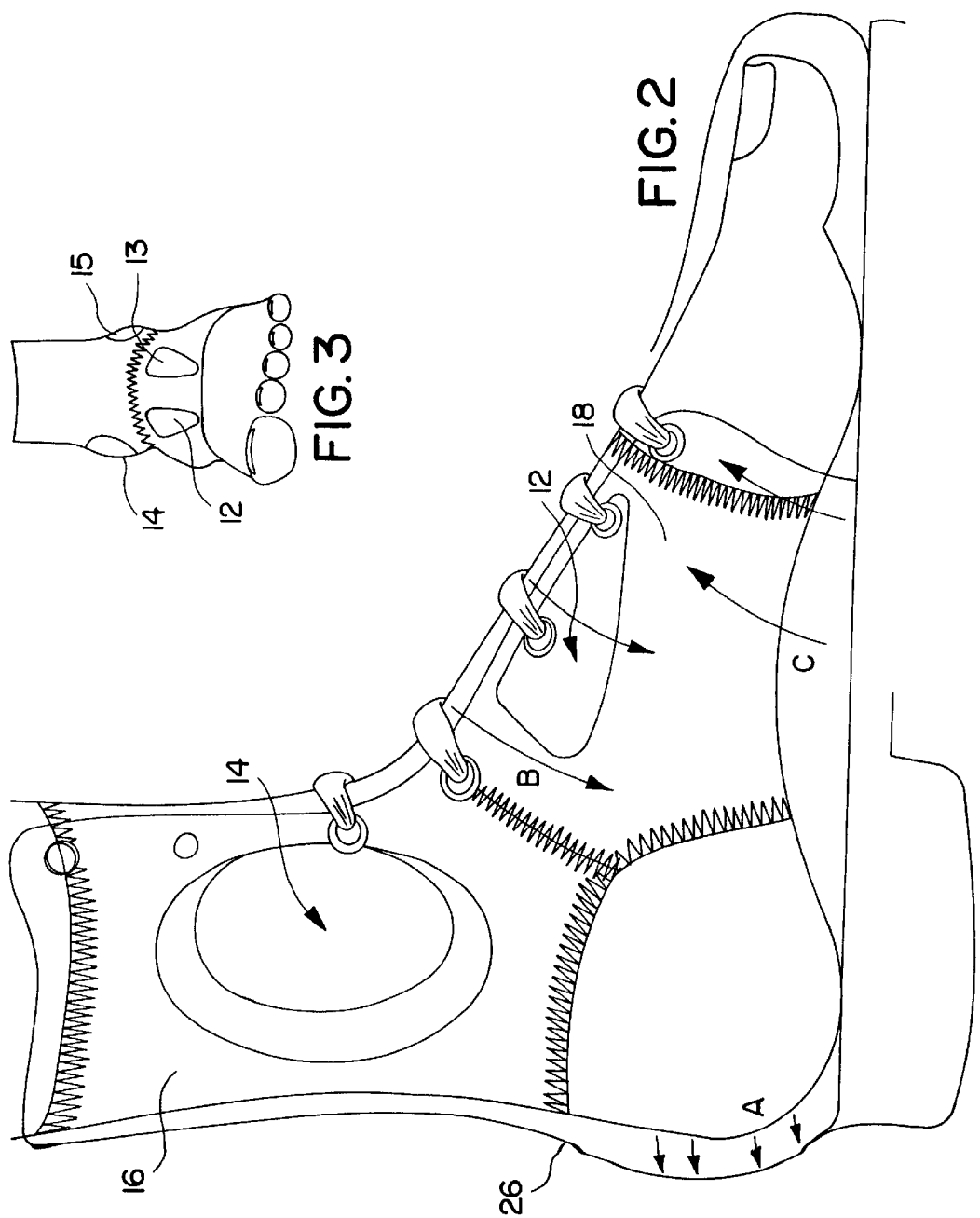

HEEL LOCKING, ENERGY ABSORBING, SUPPORT AND CUSHIONING DEVICE

FIELD OF THE INVENTION

This invention relates to an improved energy absorbing system for clothing and protective gear which are generally worn to support and/or protect the wearer, and more specifically, to socks which are adapted to support the wearer's ankle, to maintain the wearer's heel in position within footwear and to absorb impact energy applied to the foot to reduce the risk of injuries.

BACKGROUND OF THE INVENTION

Manufacturers and designers of performance footwear, which require tight and compressive lacing, strapping, buckling or attachment with a binding or other pressure or friction system of attachment, struggle to build footwear that fits well, is comfortable, provides consistent fit and is flexible enough to allow the manufactured unit to fit the many variations in sizes and shapes of feet. Manufacturers generally use layers of foams and padding materials to compensate for these natural variations, to promote comfort and protection and to universally contour the interior of the footwear to the wearer's feet. In addition to comfort and fit, the footwear must also provide support and control.

It is known that the anatomical structure of the foot causes the weight of a person to be supported at the heel and the head of the first and fifth metatarsal bones. The magnitude of forces associated with side-to-side and lateral motions, combined with the impact and shock generated by sudden stops and starts, is great in performance footwear. An athlete needs to transfer energy and weight from his or her upper body, and through the legs, ankles and feet, to generate enough energy to propel the athlete and, yet, maintain a relaxed and comfortable position to absorb the resulting shock and impact. Performance footwear is typically designed with laces, straps, binds and other pressure or friction systems of attachment in an attempt to ensure control and perfect contact between the footwear, the user's foot and any sport appliance, such as the blade of a skate, a ski or a snowboard. Other footwear, such as basketball shoes or climbing boots, includes a shaft or collar which extends over the ankles to provide support and control.

However, although the above described measures provide some support, they fail to adequately address the effect of the strong compressive forces transmitted to the instep area of the foot caused by the very lacing, strapping, buckling or other attachments used to provide the support. The measures also do not adequately or consistently maintain the user's foot in position within the footwear or boot, and more specifically, do not maintain the user's heel in a fixed and comfortable position.

At present, foam pads are generally the primary means utilized by manufacturers of supporting and cushioning apparel and other protective gear to reduce injury. However, foam merely flattens directly under the point of pressure and does not redirect the pressure or energy of the impact. Although foam acts as a shock absorber, it is incapable of acting as an energy absorber. For example, currently, the accepted remedy for "bone-out" or protruding first metatarsal bone is to use various types of foam to cushion the area. Yet, foam does not flow or conform to specific shapes. Foam merely compresses and flattens under an external load. Using foam as a cushioning material and to merely cover tender spots results in restricted circulation and does not reduce discomfort and bruising.

Shock absorbing materials such as foam compress so quickly under pressure that they are unable to absorb enough energy to significantly reduce impact trauma. Thixotropic liquids such as those described in U.S. Pat. No. 5,869,164 to Nickerson, which is a mixture of microspheres in oil and a thickener, are heavy in weight and, because they are comprise a liquid medium, they are non-compressible and therefore behave like a supporting device and do not reduce trauma or provide impact protection. As such, although shock absorbers reduce the risk of surface injury, they do not significantly reduce injury to the underlying tissues because a substantial portion of the energy is transferred to the underlying tissues. In addition, such liquid based devices are subject to puncture, susceptible to leaking and are complicated to manufacture because of their complex formulations.

In addition, although it is described in U.S. Pat. No. 5,869,164 that glass and plastic microspheres may be mixed with thixotropic liquids, the microspheres are merely suspended in the thixotropic liquid and thus are free to move around within the liquid. This freedom of movement allows the microspheres to be pushed to, and concentrated in, areas of the thixotropic liquids which are not subjected to pressure. Movement of the microspheres thus reduces the effectiveness, especially over extended periods of use, of thixotropic liquids.

Moreover, bonding agents, such as polyisobutylene polymers, which are typically used in such cushioning devices, are almost always non-liquid at room temperature because of the molecular weight, chemical composition and thermoplasticity. As such, before working with these polymers and to make them flowable, the temperature of these polymers must be raised to lower their viscosity.

Resilient, conforming materials comprising microspheres are also described in U.S. Pat. No. 4,252,910 to Schaefer. Specifically, Schaefer describes a material in which gas-filled microspheres are cohered to a mass by a bonding agent; wherein Schaefer's microspheres consist of an elastic copolymer preferably of vinylidene chloride and/or vinyl chloride copolymerized with acrylonitrile. However, the formulations of Schaefer have such a high viscosity and sticky nature make the resulting materials virtually impossible to handle and are useless for most applications. For example, Schaefer's material is non-liquid at room temperature and, according to Schaefer, the user must warm his or her foot above normal body temperature to soften Schaefer's material enough to take the shape of the user's foot. Moreover, Schaefer teaches that his material must be at least at body temperature to be flowable. In addition, Schaefer's material has a very high ratio of polymeric material to microspheres, namely, about 53:1. Furthermore, Schaefer is unable to substantially increase the number of microspheres per unit volume because of the high viscosity of Schaefer's material. The low number of microspheres in Schaefer's material severely limits the number of interstices per unit volume which, in turn, reduces the dilatent strength of Schaefer's material.

A further disadvantage of polyamide and polyisobutylene synthetic polymers as a binding agent is that the resulting cohered mass of microspheres shows a high degree of compression set (low compression regain) which limits the mass' usefulness. This is especially true when such materials are used in cushioning applications.

SUMMARY OF THE INVENTION

It is therefore a primary object of this invention to provide a device capable of absorbing impact energy for use in supportive and protective gear and apparel.

It is a further object of this invention to provide a supporting and cushioning device which, at room temperature, conforms to the user's body and compresses under pressure and yet is capable of substantial regain when the pressure is removed.

It is a further object of this invention to provide a sleeve-like device, which can be worn, much like a sock, about the foot and ankle, having one or more pockets integral with or at least partially fixed to the device which contain a semi-liquid, cushioning masma capable of absorbing impact energy.

It is a further object of this invention to provide a sock-like device to which one or more pockets or overlays are attached in a manner which does not restrict the elasticity or flexibility of the device; wherein the pockets or overlays contain pads or cells constructed of flexible, thermoplastic, heat-sealable plastic film; and wherein the flexible cells may contain one or more of the following, bonded elastic microspheres, foam, gel, liquid, gas or other suitable padding materials.

It is a further object of this invention to provide a sock-like device containing one or more cushioning packets capable of readily conforming to and around a user's foot and ankle and capable of absorbing impact energy.

It is a further object of this invention to provide a sock-like device capable of contouring itself to voids of contact to provide an improved gripping surface.

It is a further object of this invention to provide a sock-like device capable of adapting its surface shape to accommodate changing shape requirements.

It is a further object of this invention to provide a freestanding heel-lock, ankle support system which cushions and protects a user's foot and ankle from injury, absorbs impact energy, and locks the user's heel in position by flowing into, and thus filling, voids between the user's foot and ankle and the user's footwear.

It is a further object of this invention to provide a device which provides comfort, fit and cushioning across a user's instep, which pushes and maintains the position of the user's foot as far back as possible to prevent the heel from slipping, which stabilizes and maintains ankle position, to provide cushioning and support in the voids between the user's anklebone and footwear and between the user's foot and footwear.

It is a further object of the invention to provide a device, for use with various footwear, which enables the user to achieve greater unity with the footwear.

The compressive material of the invention provides numerous advantages over currently available supporting and cushioning materials. These advantages include, but are not limited to: better regain (elasticity); better impact resistance because the material of the invention absorbs a greater amount of kinetic energy because the material comprises more microspheres per unit area; better dilatency than Nickerson's dispersed microspheres which exhibit little to no dilatency; better dilatency than Schaefer's material because the material of the invention comprises a high number of microspheres per unit volume which translates into a high number of interstices per unit volume which adds to the dilatent strength of the material; decreased backpressure because energy is displaced among a greater number of microspheres; and conformation and deformation properties which are not temperature dependent.

The preferred embodiment of the heel locking, energy absorbing, support and cushioning device of the invention which is adapted to fit around at least a portion of a user's foot and ankle, generally comprises: a sleeve having one or more pockets at least partially fixed to the walls of the sleeve which are at least partially filled with a compressible, semi-liquid material capable of absorbing impact energy, comprising a plurality of microspheres bonded with long chain diisobutaines or other suitable materials which exhibit a high degree of dilatency. In applications wherein the user's foot will be subjected to pressure points associated with a first metatarsal bone and an ankle bone, one or more of the partially filled pockets are fixed to portions of the sleeve preferably correspond to and are proximate the pressure points. Pockets corresponding to the pressure points proximate the metatarsal bones, are preferably triangular in shape, and pockets corresponding pressure points proximate the ankle prominences, are preferably elliptical in shape. The sleeve may comprise an open-toe, open-heel sock.

The polymeric material and the microspheres are preferably combined in ratios of between about 10:1 to 5:1 by dry weight; wherein ratios of about 7:1 and 6:1 are preferred in the sock-like devices described herein. The polymeric material preferably comprises an ester selected from a group consisting of triethylene glycol ester or methyl ester of partially hydrogenated rosin; and may further comprise polyisobutylene, gamma-aminopropyltriethoxysilane or gamma-glycisoxypropyltrimethoxysilane. The microspheres preferably comprise polyacronitrile and polymethylmethacrylate.

Another preferred embodiment of the device of the invention, adapted to fit around at least a portion of a user's foot and ankle, comprises, a sleeve having tubular-like walls and having one or more pockets at least partially fixed to the walls of the sleeve which are at least partially filled with a compressible, polymeric material, which is flowable at room temperature, capable of absorbing impact energy, and comprises a plurality of microspheres; wherein the polymeric material and the microspheres are combined in ratios of between about 10:1 to 5:1 by dry weight; wherein the polymeric material comprises an ester selected from a group consisting of triethylene glycol ester or methyl ester of partially hydrogenated rosin; and wherein the polymeric material may further comprise polyisobutylene and gamma-aminopropyltriethoxysilane. More specifically, the ratio of polymeric material to microspheres may be about 7:1 or 6:1.

It is envisioned that the device of the invention may be adapted for use with any protective gear or apparel which is typically used to reduce pain and the risk of injuries caused by external pressure or sudden impacts. Specifically, the device is envisioned for use with ski boots; snowboarding boots; all types of skates including, but not limited to, hockey skates, figure skates, racing skates and inline skates; all types of athletic footwear including, but not limited to, soccer, basketball, rugby, football, tennis, jogging, climbing, cycling; shoes; boots; any other type of footwear; any type of orthopedic cast or brace or the like.

BRIEF DESCRIPTION OF THE DRAWINGS

Other objects, features and advantages will occur to those skilled in the art from the following description of the preferred embodiments and the accompanying drawings in which:

FIG. 1 is a view of the right side of the preferred embodiment of the invention in use around a user's foot and ankle;

FIG. 2 is a view of the right side of the preferred embodiment of FIG. 1 after the user's foot is inserted into footwear;

FIG. 3 is a front view of the preferred embodiment of FIG. 1; and

DETAILED DESCRIPTION OF THE PREFERRED EMBODIMENT

Figure 4A:
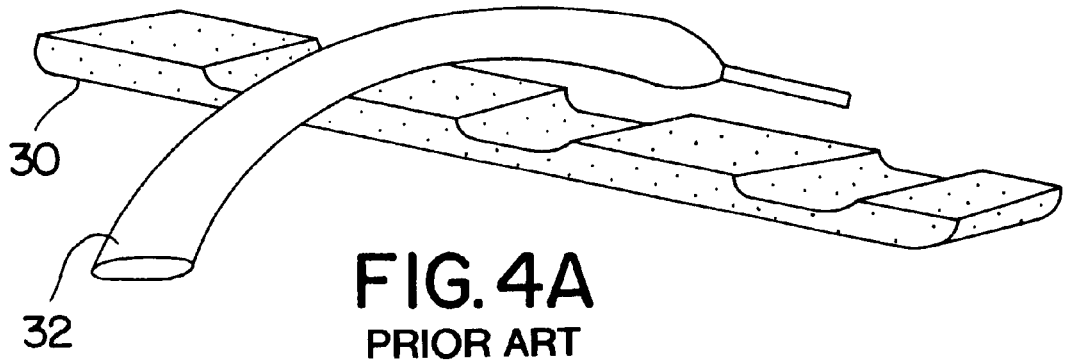
FIG. 4 is a perspective view of a foam pad of the prior art and a perspective view of a pad of the invention showing the differing response of the pads to external pressure.

The device of the invention is a sock-like device to which one or more pockets or overlays are attached in a manner which does not restrict the device's elasticity or flexibility. The pockets or overlays contain one or more pads or cells which are preferably constructed of flexible, thermoplastic, heat-sealable, plastic film. The pads or cells contain one or more of the following materials: bonded elastic microspheres, a flowable elastomer, foam, gel, liquid, gas or any other suitable padding material.

In the preferred embodiment of the device, two triangular-shaped, cushioning cells, pads or overlays are positioned on the device to protect the instep from the compressive forces, transmitted to the foot from the lacing, strapping, buckling or rigid binding. Protection is achieved by creating a bridge between the first and third metatarsal heads and distributing the compressive load. The triangular shape of the metatarsal pads, when positioned with the vertex of the triangle facing toward the front of the foot, allows the footwear or boot to be securely and comfortably tightened with laces, straps or bindings. the upward and backward action, caused by tightening the laces, straps or bindings across the instep, causes the bonded, elastic microspheres, contained in the flexible pads or cells, to change dimension and flow toward the back of the foot, which pushes the user's foot to the rear of the footwear to properly position and seat the user's heel.

Two cushioning pads, cells or overlays are also positioned over and around the ankle prominence (ankle bone) to provide additional padding and cushioning in and around the ankle. The bonded, elastic microspheres in the ankle pads provide perfect conformation to the user's ankle when the pressure applied across the user's instep pushes the user's heel to the back of the footwear. The combination of pressure and movement to the rear of the footwear causes the microspheres in the ankle pads to flow to the unoccupied areas around the ankle bone to fill any voids between the user's ankle and the shell of the footwear. The combination of the metatarsal pads pushing the user's foot backwards, and the ankle pads encasing the user ankle bone, while simultaneously filling any voids around the user's ankle, cause the user's heel to comfortably lock in a properly seated and fully cushioned position.

The heel locking, energy absorbing, support device of the invention is adapted to be worn around at least a portion of a user's foot and ankle. The device generally comprises: a sleeve having one or more pockets, which are at least partially fixed to the walls at optimal locations in the sleeve and which are at least partially filled with a compressible, semi-liquid material comprising a plurality of microspheres. The preferred embodiment of the device is adapted to be worn over or under a sock. The device may alternatively replace a sock altogether if so modified.

The preferred embodiment is shown and generally referred to in FIG. 1 as device 10. Device 10 is an open-toe, open-heel sock constructed from a power knit, elastic, support material. Device 10 is made up of foot piece 18 and ankle piece 16, two triangular-shaped pocket pieces, e.g. medial instep pad 12 and lateral instep pad 13, of a semi-liquid material are fixed to the lateral and medial sides of foot piece 18 at the instep, (FIG. 3), and two elliptical-shaped pocket pieces, e.g. medial ankle pad 14 and lateral ankle pad 15, is fixed to the lateral and medial sides of ankle piece 16, (FIG. 3).

The pads positioned on the instep mold and conform to the shape of the user's foot and fill any voids between the foot and the footwear. By filling these voids, the device increases the contact area which enables the user to achieve greater unity with the footwear.

For example, it is usually the first metatarsal bone which is the source of greatest discomfort, such as bone out problems, caused by torsion and compression experienced during activities such as skating, in-line skating, skiing and snow boarding. By placing the pads on the instep area between the second and third metatarsals on the lateral side of the instep, and placing another pad on the medial side of the first metatarsal, the protruding first metatarsal bone is bridged by the pads. The bridging action over the first metatarsal protects and cushions the instep by distributing the compressive load forces which are transmitted to the foot by lacing, strapping, buckling or attaching a rigid binding. This bridging action also causes the pressure of seating the heel to spread out and be carried by the softer tissue and tendons in the direction of arrow B.

Figure 4B:
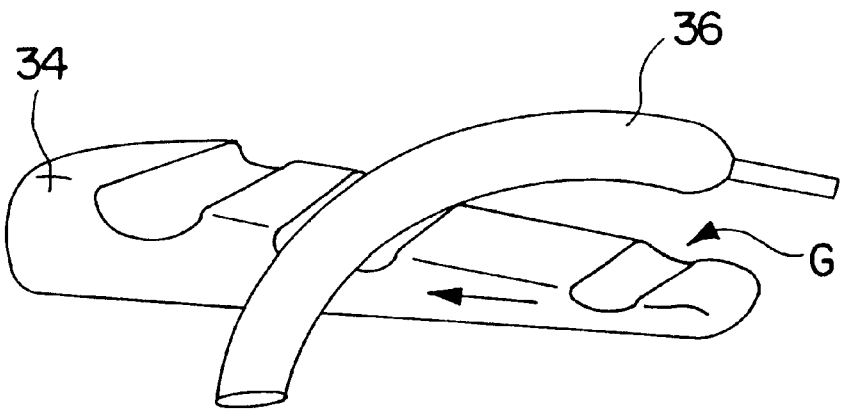

The triangular shape of the pad on the instep, as shown in FIG. 1, facilitates movement of the microspheres or content of the pad from the vertex of the triangle upward toward the base of the triangle (FIGS. 2 and 4). When footwear 26 is laced or the binding attached, the external pressure, shown in part by arrows C, causes the pad to flow and change dimension (FIG. 4). As shown in FIG. 4, the material of pad 34 of the invention flows backward toward the heel when compressed by shoelace 36, unlike the prior art foam 30, which compresses directly only under the pressure point of shoelace 32, without redirecting the pressure, and which remains compressed long after the pressure is released. This action of pad 34 pushes the foot backwards in the footwear in the direction of arrows A, (FIG. 2), thus locking the heel in place.

The pads on the instep effectively lock the heel into the back of the footwear, redirect the pressure on the first metatarsal outward and downward and redirect side to side pressure caused by the laces or binding. The redirected pressure improves control and performance and reduces pain and injury.

The elliptical-shaped ankle pads, located over the ankle bones, perform the similar function of redirecting pressure. The ankle pads effectively redirect pressure in a lateral direction, rather than from front to back. The ankle pads also conform to the shape of the user's ankle and fill the voids between the ankle and the shell of the footwear. The conforming and filling actions result in greater support and control by achieving a more intimate and complete contact between the user's ankle and the footwear. The ankle pads preferably comprise any smaller ellipse within a larger ellipse so that the inner ellipse has a larger surface area with which to contact the ankle prominence. The inner ellipse should be surrounded by a narrow band resembling a larger, elongated ellipse. The ankle pads on the lateral or outside anlde areas should be somewhat larger than the medial or inside ankle pads to accommodate the larger outer ankle prominence. The ankle pads should be positioned to define an angle of between about 10° and 45° between a horizontal line drawn through the length of the ellipse and a line drawn parallel to the bottom of the foot.

The pads or cells, in general, should be between about 3/32" and 1" thick, and preferably between about 3/32" and 1/2" thick.

To make device 10, a power knit, elastic fabric, or any other material suited to a given application, is cut into two primary pieces to form the open-toe, open-heel, sleeve-like sock of device 10 and four pocket pieces: foot piece 18, ankle piece 16, two triangular pocket pieces for pads 12 and 13, and two oval pieces for pads 14 and 15. Ankle piece 16 is of sufficient size to run up the shin from the flex point of the ankle and foot piece 18 is likewise of sufficient size to encircle the instep of the foot. Foot piece 18 is merrow stitched to ankle piece 16 at seam line 20 where the two pieces join at the flex point over the front of the ankle. The two triangular-shaped pieces are stitched to foot piece 18 and the oval-shaped pieces are stitched to ankle piece 16. The pocket pieces are preferably stitched to the wrong side of the fabric so that the pockets end up on the inside of device 10 when the device is turn right-side out. The base of the triangle pieces should be position closes to seam line 20 and are stitched along two sides of each piece and the oval pieces are positioned in an upright direction, generally perpendicular to the base of the foot and stitched part way around the perimeter of the oval to form a "C" stitch line. A packet of the compressible, semi-liquid material comprising a plurality of microspheres of the invention is inserted into each of the pockets. Once the packets are inserted, the opening of each pocket is sewn closed. The back seam 38 of ankle piece 16 is then stitched together and the bottom seam 40 of foot piece 18 is likewise stitched together, and the entire device is turned inside-out. Finally, topline 24, toe-ine 28 and the heel-line 22 are all overcast.

Alternatively, the sock of the invention may be constructed as a sock within a sock in which the pockets of elastomeric material are placed between the two sock layers and stitched into position to form a seamless surface on both the inside and outside of the sock.

The packets of the pads of the invention are preferably made by gluing, bonding or otherwise adhering gas or air filled elastic microspheres with long chain diisobutaines or other suitable materials including, but not limited to, isobutylene and/or esterified resins, stabilized or unstabilized, which exhibit a high degree of dilatency. The ratio of polymeric material to microspheres is preferably between about 10:1 to about 5:1 by dry weight. For device 10, the ratios are about 7:1 and 6:1 by dry weight. Following are four exemplary formulations of the invention. In the formulations, PAN refers to polyacrylonitrile, PMMA refers to polymethylmethacrylate and EVA refers to ethylene-vinyl acetate. The triethylene glycol ester and methyl ester of partially hydrogenated rosin is available from Hercules Inc. as Staybelite® Ester 3 Synthetic Resin or Hercolyn® D Hydrogenated Ester of rosin; the PAN/PMMA microspheres are available from Nobel Industries as Expancel DE 091; the gamma-aminopropyltriethoxysilane or gamma-glycidoxypropyltrimethoxysilane is available from Union Carbide Chemicals and Plastics Co., Inc., product numbers A-187 and A-1100, respectively; and the EVA microspheres are available from Nobel Industries as Expancel MB 092.

FIRST EXAMPLE

| | |
|---|---|
| Triethylene glycol ester or methyl ester of partially hydrogenated rosin | 500 g |
| Microspheres (PAN/PMMA) | 75 g |
| TOTAL WEIGHT | 575 g |
| Binder to microsphere ratio (dry) | 6.67:1 |

SECOND EXAMPLE

| | |
|---|---|
| Triethylene glycol ester or methyl ester of partially hydrogenated rosin | 400 g |
| Polyisobutylene | 125 g |
| Microspheres (PAN/PMMA) | 75 g |
| TOTAL WEIGHT | 600 g |
| Binder to microsphere ratio (dry) | 7.00:1 |

THIRD EXAMPLE

| | |
|---|---|
| Triethylene glycol ester or methyl ester of partially hydrogenated rosin | 400 g |
| Polyisobutylene | 125 g |
| Gamma-Aminopropylytriethoxysilane or Gamma-Glycidoxyypropyltrimethoxysilane | 10 g |
| Microspheres (PAN/PMMA) | 85 g |
| TOTAL WEIGHT | 620 g |
| Binder to microsphere ratio (dry) | 6.29:1 |

FOURTH EXAMPLE

| | |
|---|---|
| Triethylene glycol ester or methyl ester of partially hydrogenated rosin | 400 g |
| Polyisobutylene | 125 g |
| Gamma-Aminopropylytriethoxysilane or Gamma-Glycidoxyypropyltrimethoxysilane | 10 g |
| Microspheres (PAN/PMMA) | 65 g |
| Microspheres blended with EVA | 25 g |
| TOTAL WEIGHT | 625 g |
| Binder to microsphere ratio (dry) | 5.94:1 |

By coating the microspheres with non-slippery, high friction producing materials, the pads effectively exploit the rate dependent shear characteristics of the material to form a semi-liquid, conforming, energy absorbing masma. The rate of shear created by a high speed impact is substantially increased as each of the individual microspheres attempts to roll over another microsphere. Since the action of rolling over each other multiplies the applied force of shear, the resulting rate of shear at the interface of each microsphere continues to increase. This increases the inherent rate of shear to the point wherein the semi-liquid nature of the material increases its viscosity and rapidly approaches the semi-solid or solid state. The resulting solid, lightweight pad absorbs much more kinetic energy than it could in a semi-liquid state when pressure is applied in a slow, even manner. For example, the viscosity of the masma of the invention increases closer to a non-liquid, nonmovable mass as the rate of shear increases. This effect is pronounced with the high rate of shear associated with high impact blows.

The device of the invention may be modified or otherwise adapted for use as a complete sock or for use with other apparel and protective gear. Auxiliary materials may be used in connection with the device to augment the device's function and scope of use, including, but not necessarily limited to, liquids, gels and/or open or closed cell foam, or any other natural or synthetic cushioning or padding material. The shape of the pads and the overall shape and style of the device are not limited to those described above, and may be modified as needed to accommodate the application for which they are intended.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A heel locking, energy absorbing, support and cushioning device adapted to fit around at least a portion of a user's foot and ankle, comprising, a sleeve having tubular walls and having one or more pockets at least partially fixed to the walls of the sleeve which are at least partially filled with a compressible, polymeric material, which is flowable at room temperature, capable of absorbing impact energy, and comprises a plurality of microspheres, said polymeric material and said microspheres being present in a ratio of between about 10:1 to about 5:1 by dry weight.

2. The device of claim 1, wherein said user's foot is subjected to pressure at points proximate one or more metatarsal bones and one or more ankle prominences, and wherein one or more of said partially filled pockets are fixed to said sleeve at areas corresponding said pressure points.

3. The device of claim 2, wherein one or more of said pockets, corresponding to said pressure points proximate said metatarsal bones, is triangular in shape.

4. The device of claim 2, wherein one or more of said pockets, corresponding to said pressure points proximate said ankle prominences, is elliptical in shape.

5. The device of claim 4, wherein one or more of said elliptical pockets is fixed to said sleeve at one or more said areas corresponding to a pressure point proximate a lateral ankle prominence.

6. The device of claim 4, wherein one or more of said elliptical pockets is fixed to said sleeve at one or more of said areas corresponding to a pressure point proximate a medial ankle prominence.

7. The device of claim 1, wherein said sleeve comprises an open-toe, open-heel sock.

8. The device of claim 1, wherein said polymeric material and said microspheres are combined in a ratio of about 7:1 by dry weight.

9. The device of claim 1, wherein said polymeric material comprises an ester selected from a group consisting of triethylene glycol ester or methyl ester of partially hydrogenated rosin.

10. The device of claim 9, wherein said polymeric material further comprises polyisobutylene.

11. The device of claim 10, wherein said polymeric material further comprises gamma-aminopropyltriethoxysilane.

12. The device of claim 10, wherein said polymeric material further comprises gamma-glycisoxypropyltrimethoxysilane.

13. The device of claim 1, wherein one or more of said microspheres comprises polyacronitrile and polymethylmethacrylate.

14. A heel locking, energy absorbing, support and cushioning device adapted to fit around at least a portion of a user's foot and ankle, comprising, a sleeve having tubular walls and having one or more pockets at least partially fixed to the walls of the sleeve which are at least partially filled with a compressible, polymeric material, which is flowable at room temperature, capable of absorbing impact energy, and comprises a plurality of microspheres; wherein said polymeric material and said microspheres are combined in a ratio of between about 10:1 to about 5:1 by dry weight.

15. The device of claim 14, wherein said polymeric material comprises an ester selected from a group consisting of triethylene glycol ester or methyl ester of partially hydrogenated rosin.

16. The device of claim 15, wherein said polymeric material further comprises polyisobutylene and gamma-aminopropyltriethoxysilane.

17. The device of claim 16, wherein said polymeric material and said microspheres are combined in a ratio of approximately equal to or less than 6:1.

18. The device of claim 14, wherein one or more of said microspheres comprises polyacronitrile and polymethylmethacrylate.

19. The device of claim 18, wherein one or more of said microspheres further comprises ethylene-vinyl acetate.

* * * * *